(12) United States Patent
Garavani et al.

(10) Patent No.: US 7,723,390 B2
(45) Date of Patent: May 25, 2010

(54) PHARMACEUTICAL FORMULATIONS FOR THYROID HORMONES

(75) Inventors: Alberto Garavani, Ponte Capriasca (CH); Maurizio Marchiorri, Valbrona (IT); Alessandro Di Martino, Milan (IT); Angel Mateo Echanagorria, Milan (IT)

(73) Assignee: Altergon S.A., Lugano (CH)

( * ) Notice: Subject to any disclaimer, the term of this patent is extended or adjusted under 35 U.S.C. 154(b) by 621 days.

(21) Appl. No.: 10/188,467

(22) Filed: Jul. 2, 2002

(65) Prior Publication Data

US 2003/0050344 A1   Mar. 13, 2003

(30) Foreign Application Priority Data

Jul. 2, 2001 (IT) .......................... MI2001A1401

(51) Int. Cl.
- *A61K 31/198* (2006.01)
- *A61K 9/48* (2006.01)
- *A61K 9/64* (2006.01)

(52) U.S. Cl. .................. 514/567; 424/452; 424/456

(58) Field of Classification Search .............. 424/451, 424/464, 456, 463, 452; 514/567
See application file for complete search history.

(56) References Cited

U.S. PATENT DOCUMENTS

| | | | | |
|---|---|---|---|---|
| 3,157,574 A | | 11/1964 | Heming et al. ................. 167/65 |
| 3,808,332 A | * | 4/1974 | Reynolds et al. ............... 514/75 |
| 3,851,051 A | * | 11/1974 | Miskel et al. ................ 424/455 |
| 3,855,406 A | * | 12/1974 | Adams et al. ................ 424/452 |
| 4,888,239 A | * | 12/1989 | Brox ........................ 428/402.2 |
| 4,935,243 A | * | 6/1990 | Borkan et al. ................ 424/441 |
| 5,200,428 A | | 4/1993 | Horst ......................... 514/561 |
| 5,225,204 A | | 7/1993 | Chen et al. .................. 424/484 |
| 5,635,209 A | | 6/1997 | Groenewoud et al. ......... 424/464 |
| 5,814,338 A | * | 9/1998 | Veronesi ..................... 424/472 |
| 5,955,105 A | * | 9/1999 | Mitra et al. .................. 424/464 |
| 5,958,458 A | * | 9/1999 | Norling et al. ............... 424/490 |
| 5,958,979 A | | 9/1999 | Lahr et al. ................... 514/567 |
| 6,197,787 B1 | | 3/2001 | Franson et al. .............. 514/313 |
| 6,646,007 B1 | * | 11/2003 | Schreder et al. ............. 514/567 |

FOREIGN PATENT DOCUMENTS

| | | |
|---|---|---|
| EP | 0472033 | 2/1992 |
| GB | 876320 | 8/1961 |
| WO | WO 9618370 | 6/1996 |
| WO | WO 9717951 | 5/1997 |
| WO | WO 9963969 | 12/1999 |

\* cited by examiner

*Primary Examiner*—Robert A Wax
*Assistant Examiner*—Aradhana Sasan
(74) *Attorney, Agent, or Firm*—Abelman, Frayne & Schwab

(57) ABSTRACT

The present invention provides for pharmaceutical formulations based on thyroid hormones enabling a safe and stable oral administration in the framework of the strict therapeutic index prescribed in case of thyroid disorders.

10 Claims, No Drawings

PHARMACEUTICAL FORMULATIONS FOR THYROID HORMONES

FIELD OF THE INVENTION

The present invention relates to pharmaceutical compositions for thyroid hormones.

STATE OF THE ART

T3 and T4 are thyroid hormones which are used for different therapeutic applications. T3 (lyothyronine=O-(4-hydroxy-3-iodophenyl)-3,5-diiodo-L-tyrosine) and T4 (levothyroxine=O-(4-hydroxy-3,5-diiodophenyl)-3,5-diiodo-L-tyrosine), as such or in the form of sodium salts or hydrates, are broadly known and obtained by synthesis and/or extraction from animal glands (ex.: pigs, etc.).

In particular, these thyroid hormones have two important functions: they are involved in the development, in particular of the central nervous system, and in adults they act by maintaining metabolic homeostasis and by virtually influencing the function of all organs. The concentrations of thyroid hormones in serum are strictly regulated by the hormone thyrotropin through a typical negative feedback system. Anyway, the treatment of the lack of these hormones gives good results by administering T3 and T4 (or their sodium salts), and most patients can be treated by taking these hormones.

In particular, T3 and T4 are used above all in the treatment of hypothyroidism. Hypothyroidism is a very common illness. In the United States 1 baby out of 4,000-5,000 is hypothyroidic, whereas hyperthyroidism then affects 0.5-1.3% of adults. In people aged over sixty the incidence of hypothyroidism increases to reach as far as 2.7% in men and 7.1% in women. Since congenital hypothyroidism can result in irreversible mental retardation, though it can be prevented by diagnosing and treating it in its initial stages, the screening of this illness in babies is mandatory in North America, Europe and Japan.

Beyond the treatment of hypothyroidism, T4 (sodium salt of levothyroxine) can be used for example to suppress the secretion of thyrotropin in the treatment of non-endemic simple goiter, of chronic lymphocytic thyroiditis and of thyroid cancer. The sodium salt of levothyroxine is also used together with anti-thyroid agents in the treatment of thyrotoxicosis to prevent the genesis of goiter and hypothyroidism. Supplementation therapy with thyroid hormones often goes on for the whole patient's life. Moreover, the dosage should be established individually for each patient. The initial dose is generally small. The amount is then increased gradually until clinical evaluation and lab tests do not indicate an optimal response in the treated organism. The dose which is necessary to get that response is then maintained. The patient's age and his/her general physical state together with the seriousness and duration of the symptoms of hypothyroidism determine the initial dosage and the rate with which said dosage can be brought to its final level. It is particularly important to increase doses only very gradually in patients suffering from misedema and cardiovascular illnesses in order to prevent angina, myocardial infarct or ictus.

For these reasons T3 and T4, their sodium salts and their combination (Liotrix) are always administered orally, in particular by means of tablets which allow, through the control of their ingestion frequency and through the choice of dosage units, to adapt supplementation to a patient's individual situation.

As a matter of fact, a precise dosage is extremely critical since an underdosage would lead to a sub-optimal response and therefore to hypothyroidism. On the other hand, an eventual overdosage would lead to toxic symptoms of hyperthyroidism such as heart pains, palpitations or heart arrhythmias. In patients suffering from coronary illnesses even a very small increment in the dose of levothyroxine can be dangerous.

More to the point, hyperthyroidism is a known risk factor for osteoporosis. Indeed, several studies suggest that sub-clinical hyperthyroidism in pre-menopausal women undergoing a therapy with sodium salt of levothyroxine is associated with a loss of bone tissue. In order to minimize the risk of osteoporosis it is advisable to titrate the dose as much as possible until the minimum effective dose is reached. See in particular Paul, T. et al. "Long-term L-Thyroxine Therapy is associated with decreased Hip-Bone Density in Pre-Menopausal Women", *Journal of the American Medical Association*, 259:3137-3141, 1988 and also Kung, A. W. et al. "Bone Mineral Density in Pre-Menopausal Women receiving long-term Physiological Doses of Levothyroxine", *Journal of the American Medical Association*, 265:2688-2691, 1991.

Therefore, because of the risks associated with overdosage or underdosage not only of sodium salt of levothyroxine, but of thyroid hormones in general, it is absolutely critical that patients can rely on pharmaceutical products which are reliable as far as titer and bioavailability are concerned. Reaching and in particular maintaining these particularly strict criteria is therefore a great difficulty.

For instance, between 1987 and 1994 the Food and Drug Administration ("FDA") in the USA received 58 reports of irregular experiences related to the potency (titer) of products based on sodium levothyroxine administered orally. 47 of said reports suggested that the pharmaceutical preparations had a lower titer that the declared one, whereas 9 suggested that the titer was higher. Two of these reports concerned inconsistencies in the hematic level of thyroid hormones. Four of these reports resulted in hospitalization, two of which were attributed to undertitration and two to overtitration. More than half the total 58 reports were supported by hematic tests of thyroid function. Among the specific symptoms of hypothyroidism the following were reported: severe depression, tiredness, weight increase, constipation, intolerance to cold, edema and difficulty to concentrate. The specific symptoms of hyperthyroidism included atrial fibrillation, heart palpitation and insomnia.

Whereas some of these problems arose on switching the brand of the pharmaceutical product, several of them arose also when patients only bought further amounts of a product which had been administered previously for a long time with a good treatment, thus indicating a low consistency in terms of stability, titer and bioavailability among different batches of the same manufacturer.

Whereas it is known, for instance from Martindale, "The Complete Drug Reference", 1999, The Pharmaceutical Press, page 1498, that the absorption of thyroxine in the gastrointestinal area can be irregular—which causes per se a high difficulty in formulating dosage units with foreseeable and reproducible release—it appears that some of the problems related to the administration of thyroid hormones, in particular T3 and/or T4 (or of their sodium salts), are not linked only to the interaction of the administered pharmaceutical form with the patient's metabolism, but also and above all to the interaction of the active principle with the auxiliary substances contained in a given dosage unit.

As a matter of fact, it appears that for instance sodium levothyroxine is extremely sensitive to influences due to the presence of pharmaceutical excipients, though these are actually pre-selected and widely tested purposively for their inertia. As a consequence, an adequate formulation of sodium levothyroxine has always been a problem.

As discussed for instance in Hennessy, J. V. K. et al., "The Equivalency of Two L-Thyroxine Preparations", *Annals of Internal Medicine*, 102: 770-773, 1985, in 1982 a manufacturer re-formulated its product based on sodium levothyroxine by simply removing two inactive ingredients and changing the physical form of the coloring agents. During a study it has then been found that the product thus reformulated showed a high increase in titer simply because the new product contained 100% of the declared content, whereas the previous product reached only 78% (Stoffer, S. S. and W. E. Szpunar, "Potency of Levothyroxine Products.", *Journal of the American Medical Association*, 251:635-636, 1984). On the other hand, during another study it was found that the content of levothyroxine of the old formulation is reached around 70% of the declared value (Fish, L. H. et al., "Replacement Dose, Metabolism and Bioavailability of Levothyroxine in the treatment of Hypothyroidism; Role of Triiodothyronine in Pituitary Feedback in Humans," *The New England Journal of Medicine*, 316:764-770, 1987). Obviously this increase in titer involved a serious risk as far as possible occurrence of clinical problems was concerned.

Further attempts at modifying the formulations of pharmaceutical products containing levothyroxine were then made in order to obtain stable preparations. As is evident from a study carried out in 1991 (Das Gupta, V. et al., "Effect of Excipients on the Stability of Levothyroxine Sodium Tablets", *Journal of Clinical Pharmacy and Therapeutics*, 15:331-336, 1990), tablets of sodium levothyroxine from the same manufacturer, but chosen from different production batches, showed variations in their chromatograms suggesting that different excipients had been used in the preparation of the tablets.

It should be noted that, since, in 1982, the US Pharmacopeial Convention introduced the standard for a HPLC assay indicating the stability for the quality control of pharmaceutical products containing thyroid hormones, in particular T3 and T4 (Garnick, R. I. et al., "Stability Indicating High-Pressure Liquid Chromatographic Method for Quality Control of Sodium Liothyronine and Sodium Levothyroxine in Tablet Formulations" in "Hormone Drugs", J. L. Gueriguian, E. D. Bransome and A. S. Outschoorn editors, United States Pharmacopeial Convention, pages 504-516, Rockville, 1982), several products which had already been delivered have often been and are often recalled because of objections raised by the FDA.

All these problems of stability, broadly documented and repeatedly contested by the United States FDA, suggest that the current shelf-life of two years declared on the packages of many of these products is not suitable at all in the light of the high sensitivity to accelerated degradation which the active principle seems to undergo. For instance, levothyroxine is unstable in presence of light, of high temperatures, of air and of humidity (Won, C. M. "Kinetics of Degradation of Levothyroxine in Aqueous Solution and in Solid State", *Pharmaceutical Research*, 9:131-137, 1992). Moreover, during another study it has been found that some of the excipients used together with sodium levothyroxine act in turn as catalysts accelerating its degradation (Das Gupta, V. et al., "Effect of Excipients on the Stability of Levothyroxine Sodium Tablets", *Journal of Clinical Pharmacy and Therapeutics*, 15:331-336, 1990). In addition, the kinetics of degradation of sodium levothyroxine is complex. Studies conducted on stability suggest that sodium levothyroxine has a two-phase degradation profile of first order, with an initially high degradation rate, followed by a lower degradation rate (Won, C. M. "Kinetics of Degradation of Levothyroxine in Aqueous Solution and in Solid State", *Pharmaceutical Research*, 9:131-137, 1992). The initial degradation rate depends on temperature. In order to compensate initial degradation, some manufacturers use an overdosage of active principle in their formulations, thus causing among other things occasional examples of overtitration.

Finally, it is undisputed that thyroid hormones, in particular T3, T4 and their combination are a necessary treatment in many cases in which no acceptable substitutive drug exists. Nevertheless, because of the strict therapeutic index undergone by the dosage of thyroid hormones, it is particularly important that the amount of available active agent is absolutely reliable for a given pharmaceutical dosage unit. Even small variations in the actually available amount of active principle can affect both, its safety and effectiveness. Patients receiving overtitrated dosage units risk angina, tachycardia or arrhythmias. There is also evidence that an overtreatment can cause osteoporosis. In contrast thereto, undertitrated dosage units are not effective in fighting the symptoms of hypothyroidism or secondary effects.

It is also known that sodium levothyroxine is unstable in presence of ambient factors and of at least some of the commonly used pharmaceutical excipients. Nevertheless, as explained above, current formulations available on the market do not seem to solve these problems, because current products based on sodium levothyroxine and administered orally undergo titer variations before their expiry date as indicated on the package, or because they can vary from batch to batch and therefore from package to package. Because of the treatment, often lasting several decades, said deviations represent high risks as far as safety and effectiveness are concerned.

Therefore, it seems that at least since 1982 it has been known about the need to provide for pharmaceutical formulations for the preferably oral administration of thyroid hormones, in particular of T3 or T4 and of their combination, which are more reliable in terms of titer and of bioavailability. In particular, there has been for a long time the need to provide for pharmaceutical formulations for the preferably oral administration of thyroid hormones, in particular of T3 or T4 and of their combination, which are stable in time, i.e. which have an effective shelf-life of at least two years. Moreover, there is the need to provide for pharmaceutical formulations for the administration of thyroid hormones, in particular of T3 or T4 and of their combination, which allow to obtain a perfectly uniform dosage not only leaving aside the batch of manufacture, but preferably also within the pharmaceutical dosage unit itself.

The object of the present invention, therefore, is to satisfy these and other needs which will be better apparent in the following detailed description.

SUMMARY

In the framework of the present invention it has been found that the disadvantages of the prior art can be overcome by providing for pharmaceutical compositions based on thyroid hormones in capsules, preferably in soft capsules, or in swallowable (i.e. tablet-shaped or capsule-shaped) uniform soft-gel matrices.

DETAILED DESCRIPTION OF THE INVENTION

In particular, it has been found that the pharmaceutical composition in capsule, preferably in "soft capsule" or in swallowable (i.e. tablet-shaped or capsule-shaped) uniform soft-gel matrices, containing thyroid hormones, preferably T3 and/or T4, allows to obtain several advantages with respect to normal administration in known pharmaceutical forms.

Whereas the degradation of thyroid hormones in traditional solid forms of administration has been studied for a long time and by different authors, see in particular Richheimer, S. L. & Amer, T. M. "Stability-indicating assay, dissolution and content uniformity of sodium levothyroxine in tablets" *Journal of Pharmaceutical Sciences* 72(11), 1349-1351, Brower, J. F. Tolier, D. Y. & Reepmayer J. C. "Determination of sodium levothyroxine in bulk, tablet and injection formulations by high-performance liquid chromatography", *Journal of Pharmaceutical Sciences* 73(9), 1315-1317, Chong Min Wong, "Kinetics of Degradation of Levothyroxine in Aqueous Solution and in Solid State", *Pharmaceutical Research*, Vol. 9, No. 1, 1992, 131-137 and Das Gupta et al., "Effect of excipients on the stability of Levothyroxine Sodium Tablets", *Journal of Clinical Pharmacy and Therapeutics*, 15, 331-336 (1990), as seen before, it has not been possible until now—because of the plurality of potentially influent factors—to indicate a solid pharmaceutical composition and a method for its production which could overcome the aforesaid problems. For example, while it could be supposed that some pharmaceutical excipients catalyzed the decomposition of the active principle (Das Gupta et al., see above) according to a desamination reaction (Won, see above), it was also known that another pathway of decomposition consisted in a deiodization competing with the first reaction in given conditions. In practice, because of the manifold sensitivity of thyroid hormones, in particular of T3 or T4 and of their combination, none of the solid forms of administration of the prior art which consisted of tablets was particularly satisfying.

During the research work carried out for the present invention it has been found that said known negative effects of some excipients, of light, of humidity, of temperature, of the contact with oxygen, of pH, etc. as degrading factors identified and described in the prior art, are instead remarkably reduced or even eliminated by applying a method of manufacture of the form of administration which avoids the compacting of the pharmaceutical formulation typically characterizing the manufacture of tablets. The theoretical explanation as described before being provided in the present patent application without any binding intent but with mere illustrative aims, and without limiting the scope of protection requested by the applicant for the present invention, as defined only in the attached claims, it is reported that the results obtained by the inventors seem to indicate that, very likely, the degrading effect undergone by thyroid hormones, in particular T3 and/or T4, during the stress caused by the compacting stage of the semi-finished product to obtain the finished tablet, leads to an at least partial transformation of the starting thyroid hormone into an intermediate product which, once it is formed, self-catalyzes the following decomposition of the remaining active principle contained in the traditional solid pharmaceutical form, i.e. in the tablet.

As a matter of fact it has been found that the pharmaceutical forms for oral administration obtained according to the present invention are then clearly less sensitive to the various degrading influences described and discussed in the prior art. In particular, the present invention provides for pharmaceutical compositions based on thyroid hormones, in particular T3 and/or T4, in capsules, preferably in soft capsules, or in swallowable (i.e. tablet-shaped or capsule-shaped) uniform soft-gel matrices which, beyond being free from micro-contaminations that might self-catalyze the further decomposition, also determine additional advantages such as for instance the high and more immediate bioavailability of the active principle in gastric and/or intestinal environment, since said active principle is already in a dissolved/dispersed form, or anyway it is not compacted.

Traditional tablets, on the other hand, beyond disadvantages such as low titer stability described in the scientific literature as above, can result in further problems, since when they come into contact with the fluids of the gastrointestinal lumen, they dissolve quite slowly and the dissolution rate is broadly affected, beyond by the pH conditions in the lumen and the administration together with or without food, also by the specific characteristics of the tablets.

The pharmaceutical form in swallowable uniform soft-gel matrix or in capsule, preferably in soft capsule (which can be coated with an enteric layer, decomposable according to the pH value, i.e. in the desired area of the gastrointestinal tract), should it consist of a shell containing thyroid hormones, in particular T3 and/or T4, and possible excipients in solid form (for example in the case of the so-called "hard gelatin capsules" o DFC, "dry-filled capsules" as described in "Remington's Pharmaceutical Sciences", 18$^{th}$ edition, edited by Alfonso R. Gennaro, 1990, Mack Publishing Company, Easton Pa. 18042, ISBN 0-912734-04-3, or in the case of SEC, "soft elastic capsules" as described in "Remington's Pharmaceutical Sciences", 18$^{th}$ edition, edited by Alfonso R. Gennaro, 1990, Mack Publishing Company, Easton Pa. 18042, ISBN 0-912734-04-3, the latter also containing solid formulations) or in a liquid, or half-liquid vehicle, possibly together with additional excipients (i.e. in the—preferred—case of SEC; "soft elastic capsule"), or (according to a further embodiment) in case the pharmaceutical form consists of a swallowable (i.e. tablet-shaped or capsule-shaped) uniform soft-gel matrix, in which the said swallowable soft-gel matrix comprises both, the thyroid hormones and possible excipients and/or plasticers, enables a fast release of the content of the shell or of the matrix, respectively, be it hard or soft, and therefore an immediate release of the active principle which is already pulverized (in case of hard capsule—DFC—or of SEC with solid content) or already dissolved and/or dispersed (in case of soft capsules or swallowable uniform soft-gel matrices).

The enteric layers which are preferred in the framework of the present invention can be applied to all forms of capsules or swallowable uniform soft-gel matrices here described, and they are formulated according to known techniques so as to substantially decompose in the area of the small intestine which is the primary site where thyroid hormones are absorbed.

Besides (or instead of) possible enteric layers, the capsules or swallowable uniform soft-gel matrices according to the present invention can also be provided with additional outer layers which simplify ingestion, i.e. consisting of excipients which reduce the friction between the capsule and the patient's esophagus.

The materials which are used to obtain the capsules or swallowable uniform soft-gel matrices according to the present invention are common gelatins (so-called A and B type) used in the pharmaceutical field, or methylcellulose, hydroxypropylmethylcellulose, calcium alginate or other suitable materials known in the pharmaceutical art, which can also be used for the same purposes.

Moreover, the hardness of the capsules or swallowable uniform soft-gel matrices according to the present invention can be controlled according to the type of capsule or swallowable uniform soft-gel matrix which has to be obtained by means of known pharmaceutically acceptable plasticizers for capsules, such as for instance polyhydroxyl alcohols, preferably glycerol, 1,2-propylene glycol, solutions of sorbitol/sorbitanes, etc.

Further common optional components of the capsules or swallowable uniform soft-gel matrices according to the present invention are water and preserving agents (such as anti-bacterial agents, anti-fungal agents, etc.), always at the discretion of the man skilled in the art.

In particular, according to a first preferred embodiment of the present invention it is provided for a so-called hard gelatin capsule consisting of two "cases" (half-capsules) connected with each other by means of telescopic fitting, and containing thyroid hormones, preferably T3 and/or T4 or pharmaceutically acceptable salts thereof, in particular their sodium salts, in solid form mixed with common pharmaceutical excipients in form of powder, micropellets or other non-compacted microgranules. According to the various needs said micropellets or microgranules can be in turn micro-encapsulated according to known methods so as to control the release of the thyroid hormones they contain. As far as the solid excipients which can be used in this context are concerned, these are diluents, buffers, binders or disintegrating agents commonly used in the pharmaceutical field. For example, the same excipients can be used which are commonly added to obtain tablets. Some preferred examples of solid excipients are the following: dicalcium phosphate dihydrate, sodium carboxymethyl starch, microcrystalline cellulose, monohydrate lactose, sodium carboxymethylcellulose, maize starch, magnesium stearate, etc.

According to a second preferred embodiment of the present invention it is provided for a soft capsule ("soft elastic capsule") containing thyroid hormones, preferably T3 and/or T4 or pharmaceutically acceptable salts thereof, in particular their sodium salts, in solid form mixed with common pharmaceutical excipients in form of powder, micropellets or other non-compacted microgranules. According to the various needs said micropellets or microgranules can be in turn micro-encapsulated according to known methods so as to control the release of the thyroid hormones they contain. As far as the solid excipients which can be used in this context are concerned, these are diluents, binders or disintegrating agents commonly used in the pharmaceutical field. For example, the same excipients can be used which are commonly added to obtain tablets. Some preferred examples of solid excipients are the following: dicalcium phosphate dihydrate, sodium carboxymethyl starch, microcrystalline cellulose, monohydrate lactose, sodium carboxymethylcellulose, maize starch, magnesium stearate, etc.

According to "Remington's Pharmaceutical Sciences", 18$^{th}$ edition, edited by Alfonso R. Gennaro, 1990, Mack Publishing Company, Easton Pa. 18042, ISBN 0-912734-04-3, the soft capsules containing solid formulations according to the present invention can be obtained with the so-called "Accogel Capsule machines" o "Stern" machines developed by Lederle. Another machine and method to obtain soft capsules containing solid formulations according to the present invention are described in U.S. Pat. No. 5,740,660 of Scherer Corp.

According to a third embodiment of the present invention, which is particularly preferred, it is also provided for a soft capsule (SEC) consisting of a shell of gelatin material containing thyroid hormones, preferably T3 and/or T4 or pharmaceutically acceptable salts thereof, in particular their sodium salts, and possible excipients in a liquid or half-liquid vehicle. In particular, said soft capsule contains an inner phase consisting of a liquid, a half-liquid, a paste, a gel, an emulsion or a suspension comprising the liquid (or half-liquid) vehicle and the thyroid hormones together with possible excipients in suspension or solution.

The preferred manufacturing process for the soft capsule as described above provides for the dissolution/suspension of the active principle and of possible excipients in the liquid or half-liquid vehicle to give an inner phase which is then injected into the melted gelatin semi-finished product so as to obtain the finished capsule. Anyway, any known method described in the pharmaceutical literature to obtain SEC with liquid or half-liquid content, such as for instance the "Plate Process", the "Rotary Die Process" or the use of the "Norton Capsule Machine" or of the same "Accogel Capsule Machine" as described in "Remington's Pharmaceutical Sciences", 18$^{th}$ edition, edited by Alfonso R. Gennaro, 1990, Mack Publishing Company, Easton Pa. 18042, ISBN 0-912734-04-3, can be applied in order to obtain soft capsules according to the present invention comprising thyroid hormones and possible excipients in a liquid or half-liquid vehicle.

It should be observed that, in the specific case providing for the use of solutions of thyroid hormones dissolved in the liquid or half-liquid vehicle contained in the soft capsules, this preferred embodiment of the present invention involves also an additional advantage, i.e. the relative case in obtaining dosage units which are perfectly homogeneous one with the other, especially if compared with the very laborious methods to prepare perfectly homogeneous solid mixtures. As a matter of fact, the known machines for the production of SEC with liquid or half-liquid content enable the microdosage of the content (i.e. of the inner phase) with such a precision that the variation of content from capsule to capsule is within one percent or less.

Among the excipients which can be used together with liquid vehicles one can quote all common pharmaceutically acceptable solid additives which can be used, dispersed or dissolved, to modify the viscosity of the capsule content or the release profile of thyroid hormones from the vehicle. Further excipients which can be added to the vehicle contained in the soft capsule are preserving agents such as parabens, preferably methyl para-hydroxybenzoate, ethyl para-hydroxybenzoate or propyl para-hydroxybenzoate or their salts.

Among the liquid or half-liquid vehicles one can quote as mere examples glycerol, ethanol, polyethylene glycol (particularly with a molecular weight of 200-800), glycofurol (tetrahydrofurfuryl alcohol polyethylene glycol ether; Sigma T3396), 1,2-propylene glycol, pharmaceutically acceptable oils, or non-ionic surfactants, for example polysorbates (polysorbate 20 or 80), or various Tweens® (i.e. monolaurates, monooleates, monopalmitates, monostearates, polyoxyethylene sorbitane trioleates or tristearates, for example Tween® 80, Sigma P1754) or other vehicles (or their mixtures) which are commonly used in the pharmaceutical field to prepare SEC with liquid or half-liquid content.

A preferred example of the capsule material is gelatin (both of A type and obtained from pigs' skins, animal bones or fish by acid treatment, and of B type and obtained from animal bones and skins by alkali treatment), whereas the plasticizers which can be used to control the elasticity of the capsule can be glycerol, 1,2-propylene glycol, 85% solution of sorbitol/sorbitanes, etc. As is known in the pharmaceutical field, the gelatin material and the liquid or half-liquid content of the capsule should be compatible, and therefore, as far as the capsule material is concerned, it is preferable to use plasticizers which are also present (possibly in different percentages) in the liquid or half-liquid vehicle, for example glycerol. Among the possible formulations according to the third embodiment of the invention, SEC capsules comprising thyroid hormones or pharmaceutically acceptable salts thereof, in particular their sodium salts in a liquid or a half liquid vehicle consisting of ethanol or glycerol or of a mixture of ethanol and glycerol and possible excipients in suspension or solution are particularly preferred.

According to a first preferred formulation embraced by the third embodiment of the invention, an SEC capsule containing a liquid or half-liquid inner phase comprising thyroid hormones or pharmaceutically acceptable salts thereof, in particular their sodium salts in a liquid or half liquid vehicle consisting of ethanol or glycerol or of a mixture of ethanol and glycerol is provided.

According to a second preferred formulation embraced by the third embodiment of the invention, an SEC capsule containing an inner phase consisting of a paste or gel comprising gelatin and thyroid hormones or pharmaceutically acceptable salts thereof, in particular their sodium salts in a liquid or half liquid vehicle consisting of ethanol or glycerin or of a mixture of ethanol and glycerol is provided.

According to a fourth embodiment of the invention, swallowable (i.e. tablet-shaped or capsule-shaped) uniform soft-gel matrices are provided, in which the said soft-gel matrix comprises both, the thyroid hormones, in particular T3 and/or T4 or pharmaceutically acceptable salts thereof, in particular their respective sodium salts, and possible excipients and/or plasticers. Accordingly, these swallowable uniform soft-gel matrices of the invention are constituted of a single phase and are as such not provided (except for putative external additive layers like enteric layers or layers facilitating the swallowing) with an outer shell which could be distinguished from the bulk of the soft-gel matrix. Methods of manufacture of uniform soft gel matrices are available in the pharmaceutical art and/or in food technology.

A preferred but in no way exclusive process of manufacture of the said swallowable uniform soft-gel matrix comprises the dissolution/suspension of the active ingredient and of eventual excipients and/or plasticizers in a liquid vehicle (preferably chosen from glycerol or glycerol/ethanol mixtures) which is then gelled through addition of gelatin (or of a vehicle/gelatin premix of high gelatin content) to give a gelled mass from which the final tablet-shaped or capsule-shaped matrices are obtained preferably through heat melting and subsequent molding, e.g. injection molding. A further advantageous feature of the said swallowable uniform soft-gel matrices thus obtained arises from the fact that the same can be divided—at least in case the same are not provided with enteric coatings or the like—upon a physician's recommendation by the patient himself (eg. into two halfs or into three thirds) to allow for a further fine-tuning of the daily dosage beyond the standard dosage units provided by the pharmaceutical manufacturer. Moreover, as pointed out earlier, in all of the cases in which solutions of the active ingredient(s) are employed in the obtaining of the gel matrix, the production of perfectly homogeneous dosage units is particularly eased.

Among the optional excipients which may possibly assist in the preparation of the swallowable uniform soft-gel matrix, one should list the "usual" pharmaceutically acceptable components like e.g. solid additives acting as thickeners which may become dissolved or dispersed in the liquid vehicle prior to or during gelification of the matrix and/or preservatives like e.g. parabenes, preferably methyl parahydroxy benzoate, ethyl para ethyl parahydroxy bezoate or propyl parahydroxy benzoate or their salts.

Preferred vehicles are chosen among glycerol, ethanol, polyethylene glycol or their mixtures, glycerol and glycerol/ethanol mixtures being particularly preferred. As non-limiting examples for the gelatin, again type A or B are preferred, whereas plasticers (like sorbitol/sorbitanes or glycerol) may be added to modify the elasticity of the soft-gel, exclusively in case that the vehicles and/or excipients already mentioned above are not sufficient to obtain the desired result.

In particular, also in the case of the swallowable uniform softgel matrices, substances providing for multiple functions like e.g. glycerol (acting as vehicle and/or plasticizer) are particularly preferred.

EXPERIMENTAL PART

The following lists some examples of formulations according to the present invention:

I. Hard capsules (DFC) with solid content:
Example 1: hard gelatin capsule containing a granulate consisting of T4, dicalcium phosphate dihydrate, sodium carboxymethyl starch, microcrystalline cellulose and magnesium stearate.
Example 2: hard hydroxypropylmethylcellulose capsule (+optional coloring agents) containing a granulate consisting of T3, calcium phosphate dihydrate ($CaHPO_4 \cdot 2H_2O$), sodium carboxymethyl starch, microcrystalline cellulose and magnesium stearate.
Example 3: hard gelatin capsule (+optional coloring agents) containing a granulate consisting of T4, monohydrate lactose, sodium carboxymethylcellulose, microcrystalline cellulose and magnesium stearate.
Example 4: hard gelatin capsule (+optional coloring agents) containing a granulate consisting of T3 and T4, maize starch sodium carboxymethylcellulose, microcrystalline cellulose and magnesium stearate.

II. Soft capsules (SEC) with solid content:
The solid contents of these capsules can be the same as in the case of hard capsules as described above.

III. Soft capsules (SEC) with liquid, half-liquid, paste-like or gel-like inner phase:
The following compositions and percentages refer to the whole dried capsule, i.e. soft shell and its content:

|  | % by weight |
|---|---|
| Example 1 | |
| $T_3$ Na | 0.001-1% |
| Glycerol | 5-30% |
| Ethanol | 1-15% |
| Polyethylene glycol 400 | 20-90% |
| Gelatin | 3-40% |
| Water | 1-10% |
| 85% solution of sorbitol/sorbitanes | 0.5-30% |
| Example 2 | |
| $T_4$ Na | 0.001-1% |
| Glycerol | 5-30% |
| Ethanol | 1-15% |
| Polyethylene glycol 400 | 20-90% |
| Gelatin | 3-40% |
| Water | 1-10% |
| 85% solution of sorbitol/sorbitanes | 0.5-30% |
| Example 3 | |
| $T_3$ Na | 0.001-1% |
| Glycerol | 5-30% |
| Ethanol | 5-15% |

|  | % by weight |
|---|---|
| Tween 80 | 20-90% |
| Gelatin | 3-40% |
| Water | 1-10% |
| 85% solution of sorbitol/sorbitanes | 0.5-30% |
| *Example 4* | |
| T₄ Na | 0.001-1% |
| Glycerol | 5-30% |
| Ethanol | 5-15% |
| Tween 80 | 20-90% |
| Gelatin | 3-40% |
| Water | 1-10% |
| 85% solution of sorbitol/sorbitanes | 0.5-30% |
| *Example 5* | |
| T₃ Na | 0.001-1% |
| Glycerol | 1-30% |
| Ethanol | 1-10% |
| Water | 1-10% |
| Polyethylene glycol 300 | 15-90% |
| Gelatin | 3-40% |
| 85% solution of sorbitol/sorbitanes | 0.5-30% |
| *Example 6* | |
| T₄ Na | 0.001-1% |
| Glycerol | 1-30% |
| Ethanol | 1-10% |
| Water | 1-10% |
| Polyethylene glycol 300 | 15-90% |
| Gelatin | 3-40% |
| 85% solution of sorbitol/sorbitanes | 0.5-30% |
| *Example 7* | |
| T₃ Na | 0.001-1% |
| Glycerol | 1-30% |
| Ethanol | 1-10% |
| Water | 1-10% |
| Gelatin | 3-40% |
| Polyethylene glycol 600 | 10-60% |
| *Example 8* | |
| T₄ Na | 0.001-1% |
| Glycerol | 1-30% |
| Ethanol | 1-10% |
| Water | 1-10% |
| Gelatin | 3-40% |
| Polyethylene glycol 600 | 10-60% |
| *Example 9* | |
| T₃ Na | 0.001-1% |
| T₄ Na | 0.001-1% |
| Glycerol | 1-30% |
| Ethanol | 1-10% |
| Gelatin | 3-40% |
| Polyethylene glycol 400 | 20-80% |
| Water | 1-10% |
| Methyl para-hydroxybenzoate | 0.01-1% |
| Propyl para-hydroxybenzoate | 0.01-1% |
| *Example 10* | |
| T₃ Na | 0.001-1% |
| T₄ Na | 0.001-1% |
| Glycerol | 1-30% |
| Ethanol | 1-10% |
| Gelatin | 3-40% |
| Polyethylene glycol 400 | 20-80% |
| *Example 11* | |
| T₃ Na | 0.001-1% |
| T₄ Na | 0.001-1% |
| Glycerol | 1-30% |

|  | % by weight |
|---|---|
| Ethanol | 1-10% |
| Gelatin | 3-40% |
| Polyethylene glycol 600 | 10-90% |
| Water | 1-10% |
| 85% solution of sorbitol/sorbitanes | 0.5-30% |
| *Example 12* | |
| T₄ Na | 0.001-1% |
| Tween 80 | 20-95% |
| Gelatin | 3-40% |
| 85% solution of sorbitol/sorbitanes | 1-30% |
| Glycerol | 1-30% |
| Water | 1-10% |
| Methyl para-hydroxybenzoate | 0.01-1% |
| Propyl para-hydroxybenzoate | 0.01-1% |
| *Example 13* | |
| T₄ Na | 0.001-1% |
| Gelatin | 20-95% |
| Glycerol | 1-40% |
| Water | 1-30% |
| *Example 14* | |
| T₄ Na | 0.001-1% |
| Gelatin | 20-95% |
| Glycerol | 1-40% |
| Ethanol | 0.1-50% |
| Water | 0.1-10% |
| *Example 15* | |
| T₃ Na | 0.001-1% |
| Gelatin | 20-95% |
| Glycerol | 1-40% |
| Ethanol | 0.1-50% |
| Water | 0.1-10% |

The following compositions and percentages refer to the inner phase injected into the SEC capsules:

|  | % by weight |
|---|---|
| *Example A* | |
| T₄ Na | 0.001-1% |
| Ethanol | 1-10% |
| Glycerol | 1-30% |
| Polyethylene glycol 400 | q.s. ad 100% |
| *Example B* | |
| T₄ Na | 0.001-1% |
| Ethanol | 1-10% |
| Glycerol | 1-30% |
| Tween 80 | q.s. ad 100% |
| *Example C* | |
| T₄ Na | 0.001-1% |
| Tween 80 | q.s. ad 100% |
| *Example D* | |
| T₄ Na | 0.001-1% |
| Polyethylene glycol 400 | q.s. ad 100% |
| *Example E* | |
| T₄ Na | 0.001-1% |
| Ethanol | 1-10% |
| Propylene glycol | 1-30% |
| Polyethylene glycol 400 | q.s. ad 100% |

-continued

| | % by weight |
|---|---|
| Example F | |
| $T_4$ Na | 0.001-1% |
| Gylcerol | 1-20% |
| Polyethylene glycol 400 | q.s. ad 100% |
| Example G | |
| $T_4$ Na | 0.001-1% |
| Glycofurol | q.s. ad 100% |
| Example H | |
| $T_4$ Na | 0.001-1% |
| Polyethylene glycol 300 | q.s. ad 100% |
| Example I | |
| $T_4$ Na | 0.001-1% |
| Ethanol | 0.1-50% |
| Glycerol | q.s. ad 100% |
| Example K | |
| $T_3$ Na | 0.001-1% |
| Ethanol | 0.1-50% |
| Glycerol | q.s. ad 100% |
| Example L | |
| $T_4$ Na | 0.001-1% |
| Ethanol | 0.1-50% |
| Gelatin | 0.1-20% |
| Glycerol | q.s. ad 100% |
| Example M | |
| $T_3$ Na | 0.001-1% |
| Ethanol | 0.1-50% |
| Gelatin | 0.1-20% |
| Glycerol | q.s. ad 100% |
| Example N | |
| $T_4$ Na | 0.001-1% |
| $T_3$ Na | 0.001-1% |
| Ethanol | 0.1-50% |
| Gelatin | 0.1-30% |
| Glycerol | q.s. ad 100% |
| Example O | |
| $T_3$ Na | 0.001-1% |
| Gelatin | 0.1-30% |
| Glycerol | q.s. ad 100% |
| Example P | |
| $T_4$ Na | 0.001-1% |
| Gelatin | 1-30% |
| Glycerol | q.s. ad 100% |
| Example Q | |
| $T_4$ Na | 0.001-1% |
| Water | 0.1-40% |
| Ethanol | 0.1-50% |
| Glycerol | q.s. ad 100% |
| Example R | |
| $T_4$ Na | 0.001-1% |
| Gelatin | 1-30% |
| Water | 0.1-40% |
| Glycerol | q.s. ad 100% |
| Example S | |
| $T_4$ Na | 0.001-1% |
| Gelatin | 1-30% |
| Water | 0.1-40% |
| Ethanol | 0.1-50% |
| Glycerol | q.s. ad 100% |
| Example T | |
| $T_3$ Na | 0.001-1% |
| Gelatin | 1-30% |

-continued

| | % by weight |
|---|---|
| Water | 0.1-40% |
| Ethanol | 0.1-50% |
| Glycerol | q.s. ad 100% |
| Example U | |
| $T_3$ Na | 0.001-1% |
| $T_4$ Na | 0.001-1% |
| Gelatin | 1-30% |
| Water | 0.1-40% |
| Ethanol | 0.1-50% |
| Glycerol | q.s. ad 100% |

IV. The following compositions and percentages refer to swallowable uniform soft-gel matrices according to the invention, in the dried state:

| Example V | % by weight |
|---|---|
| $T_4$ Na | 0.001-1% |
| Glycerol | 1-30% |
| Gelatin | q.s. ad 100% |

The invention claimed is:

1. A pharmaceutical composition comprising thyroid hormones or their sodium salts in the form of either:
   a) a soft elastic capsule consisting of a shell of gelatin material containing a liquid or half-liquid inner phase comprising said thyroid hormones or their salts in a range between 0.001 and 1% by weight of said inner phase, dissolved in gelatin and/or glycerol, and optionally ethanol, said liquid or half-liquid inner phase being in direct contact with said shell without any interposed layers, or
   b) a swallowable uniform soft-gel matrix comprising glycerol and said thyroid hormones or their salts in a range between 0.001 and 1% by weight of said matrix.

2. The composition according to claim 1, wherein said thyroid hormones are selected from the group consisting of T3, T4 and their sodium salts.

3. The composition according to claim 1, wherein said swallowable uniform soft-gel matrix further comprises gelatin of A type or B type.

4. The composition according to claim 1, wherein said liquid or half-liquid inner phase of said soft elastic capsules comprises a vehicle consisting of ethanol, glycerol or mixtures thereof.

5. The composition according to claim 1, wherein said swallowable uniform soft gel matrix comprises a glycerol/ethanol mixture.

6. The pharmaceutical composition according to claim 1, having an enteric coating enabling the release of thyroid hormones in the small intestine.

7. The pharmaceutical composition according to claim 1, having an outer coating which simplifies ingestion.

8. The pharmaceutical composition according to claim 1, wherein the material of the capsule contents or the swallowable uniform soft-gel matrix includes a plasticizer to control its hardness.

9. The pharmaceutical composition according to claim 8, wherein said plasticizer is selected from the group consisting of glycerol, 1,2-propylene glycol, a solution of sorbitol/sorbitanes and combinations thereof.

10. A pharmaceutical composition according to claim 1, wherein said liquid or half-liquid inner phase comprises gelatin, glycerol and ethanol.

* * * * *

UNITED STATES PATENT AND TRADEMARK OFFICE
CERTIFICATE OF CORRECTION

PATENT NO. : 7,723,390 B2  
APPLICATION NO. : 10/188467  
DATED : May 25, 2010  
INVENTOR(S) : Alberto Garavani et al.

Page 1 of 1

It is certified that error appears in the above-identified patent and that said Letters Patent is hereby corrected as shown below:

In the Specification

Column 6, Line 28, replace "half-liquid" with --semi-liquid--

Column 7, Lines 64 and 66, replace "half-liquid", each occurrence, with --semi-liquid--

Column 7, Line 67 to Column 8, Line 1, replace "half-liquid" with --semi-liquid--

Column 8, Lines 6, 10, 18, 22, 29, 43, 54, 62, and 66, replace "half-liquid", each occurrence, with --semi-liquid--

Column 9, Lines 3, 11, and 18-19, replace "half liquid", each occurrence, with --semi-liquid--

Column 9, Line 9, replace "half-liquid" with --semi-liquid--

Column 10, Line 38, replace "half-liquid" with --semi-liquid--

In the Claims

In Claim 1, at Column 14, Lines 34 and 38, replace "half-liquid", each occurrence, with --semi-liquid--

In Claim 4, at Column 14, Line 52, replace "half-liquid" with --semi-liquid--

In Claim 10, at Column 16, Line 2, replace "half-liquid" with --semi-liquid--

Signed and Sealed this  
Ninth Day of March, 2021

Drew Hirshfeld  
*Performing the Functions and Duties of the*  
*Under Secretary of Commerce for Intellectual Property and*  
*Director of the United States Patent and Trademark Office*